(12) United States Patent
Pietras et al.

(10) Patent No.: US 6,699,843 B2
(45) Date of Patent: Mar. 2, 2004

(54) METHOD FOR TREATMENT OF TUMORS USING NUCLEIC ACID LIGANDS TO PDGF

(75) Inventors: Kristian Pietras, Uppsala (SE); Arne Östman, Uppsala (SE); Carl-Henrik Heldin, Uppsala (SE); Kristofer Rubin, Uppsala (SE)

(73) Assignee: Gilead Sciences, Inc., Foster City, CA (US)

( * ) Notice: Subject to any disclaimer, the term of this patent is extended or adjusted under 35 U.S.C. 154(b) by 205 days.

(21) Appl. No.: 09/859,724

(22) Filed: May 17, 2001

(65) Prior Publication Data

US 2002/0034506 A1 Mar. 21, 2002

Related U.S. Application Data

(63) Continuation-in-part of application No. 08/991,743, filed on Dec. 16, 1997, now Pat. No. 6,229,002, which is a continuation-in-part of application No. 08/618,693, filed on Mar. 20, 1996, now Pat. No. 5,723,594, which is a continuation-in-part of application No. 08/479,783, filed on Jun. 7, 1995, now Pat. No. 5,668,264, which is a continuation-in-part of application No. 08/479,725, filed on Jun. 7, 1995, now Pat. No. 5,674,685.

(60) Provisional application No. 60/205,006, filed on May 17, 2000.

(51) Int. Cl.$^7$ .......................... A61K 31/70; C12Q 1/68; C12P 19/34; C07H 21/04; C07H 21/02

(52) U.S. Cl. ........................... 514/44; 435/6; 435/91.2; 436/501; 536/23.1; 536/24.33; 536/25.4

(58) Field of Search .................... 435/6, 91.2; 514/44; 424/1.73; 536/23.1, 24.33, 25.4, 22.1; 436/501

(56) References Cited

U.S. PATENT DOCUMENTS

| | | | |
|---|---|---|---|
| 4,683,195 A | | 7/1987 | Mullis et al. |
| 4,711,955 A | | 12/1987 | Ward et al. |
| 4,828,979 A | | 5/1989 | Klevan et al. |
| 4,935,363 A | | 6/1990 | Brown et al. |
| 5,070,010 A | | 12/1991 | Hsu |
| 5,270,163 A | | 12/1993 | Gold et al. |
| 5,475,096 A | | 12/1995 | Gold et al. |
| 5,476,766 A | | 12/1995 | Gold et al. |
| 5,502,037 A | * | 3/1996 | Kondratyev |
| 5,595,877 A | | 1/1997 | Gold et al. |
| 5,756,291 A | * | 5/1998 | Griffin et al. |
| 6,229,002 B1 | | 5/2001 | Janjic et al. ............ 536/23.1 |

FOREIGN PATENT DOCUMENTS

| | | |
|---|---|---|
| GB | 2 183 661 | 6/1987 |
| WO | WO 89/06694 | 7/1989 |
| WO | WO 91/19813 | 12/1991 |
| WO | WO 92/05285 | 9/1992 |
| WO | WO 92/14843 | 9/1992 |

OTHER PUBLICATIONS

Uhrbom et al. (Feb. 2000) *Int. J. Cancer* 85:398–406.
Powis and Kozikowski (Oct. 1991) *Clin Biochem.* 24:385–397.
Pietras et al. (Apr. 2001) Cancer Research 61:2929–2934.
PUBMED Aids Alert (Jun. 1996) 11(6):67–68.
Andrake et al. (1988) *Proc. Natl. Acad. Sci. USA* 85:7942–7946.
Bass and Cech (1984) *Nature* 308:820–826.
Betsholtz et al. (1984) *Cell* 39:447–457.
Bock et al. (1992) *Nature* 355:564–566.
Buchdunger et al. (1995) *Proc. Natl. Acad. Sci. USA* 92:2558–2562.
Carey et al. (1983) *Biochemistry* 22:2601–2610.
Cohen et al. (1969) *Proc. Natl. Acad. Sci.* USA. 63:458–464.
Duan et al. (1991) *J. Biol. Chem.* 266:413–418.
Ellington and Szostak (1990) Cold Spring Harbor, NY p. 84.
Ellington and Szostak (1990) *Nature* 346:818–822.
Engstrom et al. (1992)*J. Biol. Chem.* 267:16581–16587.
Ferns et al. *Science* (1991) 253:1129–1132.
Floege et al. (1999) *Am. J. Pathol.* 154:169–179.
Green et al. (1996) Biochemistry 35:14413–14424.
Herren et al. (1993) *Biochimica et Biophysica Acta* 1173:294–302.
Jain (1996) Science 271:1079–1080.
Johnsson et al. (1985) *Proc. Natl. Acad. Sci. USA* 82:1721–1725.
Joyce (1989) Gene 82:83–87.
Joyce and Inoue (1989) Nucleic Acids Research 17:711–722.
Kacian et al. (1972) *Proc. Natl. Acad. Sci. USA* 69:3038–3042.
Kinzler and Vogelstein (1989) Nucleic Acids Research 17:3645–3653.
Kovalenko et al. (1994) *Cancer Research*, 54:6106–6114.
Kramer (1974) J. Mol. Biol. 89:719–736.
Kristjansen et al. (1993) Cancer Res. 53:4764–4766.
Kristensen et al. (1996) Br. J. Cancer 74: 533–536.
Lee et al. (1992) Cancer Res. 52:3237–3240.
Lestienne et al. (1983) *Biochime* 65:49–52.
Levisohn and Spiegleman (1968) *Proc. Natl. Acad. Sci.* USA 60:866–872.

(List continued on next page.)

Primary Examiner—S Zitomer
(74) Attorney, Agent, or Firm—Swanson & Bratschun, LLC

(57) ABSTRACT

A method is provided for treating solid tumors comprising administering a composition comprising a PDGF aptamer and a cytotoxic agent. In a preferred embodiment the PDGF aptamer is identified using the SELEX process for the Systematic Evolution of Ligands by Exponential enrichment. A method is also provided for reducing the interstitial fluid pressure (IFP) of a solid tumor comprising administering a PDGF aptamer. Finally, a method is provided for increasing the uptake of cytotoxic agents into a tumor comprising administering a composition comprising a PDGF aptamer and a cytotoxic agent.

11 Claims, 6 Drawing Sheets

OTHER PUBLICATIONS

Levisohn and Spiegleman (1969) *Proc. Natl. Acad. Sci.* USA 63:805–811.
Ma and Ptashne (1987) *Cell* 51:113–119.
MacKellar et al. (1992) *Nucleic Acids Research* 20:3411–3417.
Maniatis et al. (1982) *Molecular Cloning: A Laboratory Manual*, Cold Spring Harbor, NY., p. 118.
Maniatis et al. (1987) *Science* 236:1257–1245.
Matthews and Kricka (1988) *Analytical Biochemistry* 169:1–25.
Miele et al. (1983) *J. Med. Biol.* 171:281–295.
Mills et al. (1967) Proc. Natl. Acad. Sci. USA 58:217–220.
Mills et al. (1973) *Science* 180:916–927.
Min et al. (1988) *Nucleic Acids Res.* 16:5075–5088.
Muesing et al. (1985) Nature 313:450–457.
Oliphant and Struhl (1987) *Methods in Enzymology* 155:568–582.
Oliphant and Struhl (1988) *Nucleic Acids Research* 16:7673–7683.
Oliphant et al. (1986) *Gene* 44:177–183.
Oliphant et al. (1989) *Mol. Cell. Biol.* 9:2944–2949.
Orgel (1979) *Proc. R. Soc. Lond.* B205:435–442.
Ou et al. (1988) *Science* 239:295–297.
Rich et al. (1984) *Ann. Rev. Biochem.* 53:791–846.
Robertson and Joyce (1990) *Nature* 344:467–468.
Romaniuk et al. (1987) *Biochemistry* 26:1563–1574.
Saffhill et al. (1970) *J. Mol. Biol.* 51:531–539.
Schimmel (1989) *Cell* 58:9–12.
Stein et al. (1993) *Science* 261:1004–1012.
Szostak (1988) (S.A. Benner ed.) Springer–Verlag Berlin Heidelberg, pp. 87–113.
Thiesen and Bach (1990) *Nucleic Acids Res.* 18:3203–3208.
Tiesman and Hart (1993) *J. Biol. Chem.* 268:9621–9628.
Tuerk and Gold (1990) *Science* 249:505–510.
Tuerk et al. (1988) *Proc. Natl. Acad. Sci.* USA 85:1364–1368.
Uhlenbeck et al. (1983) *J. Biomolecular Structure and Dynamics* 1:539–552.
Vassbotn et al. (1992) *J. Biol. Chem.* 267:15635–15641.
Vassbotn et al. (1994) *J. Cell Physiol.* 158:381–389.
Watson et al. (1987) *Molecular Biology of the Gene*, Benjamin/Cummings Publishing Co., Inc., CA., pp. 267, 295, 323, 361, 394, 396, 397, and 405.
Williams et al. (1984) *J. Biol. Chem.* 259:5287–5294.
Witherell and Uhlenbeck (1989) *Biochemistry* 28:71–76.
Yarus (1988) *Science* 240:1751–1758.

\* cited by examiner

NX31975  40K PEG

SEQ ID NO:1

U at positions 6, 20 and 30 is 2'-fluoro-2'-deoxyuridine.
C at positions 8, 21, 28, and 29 is 2'-fluoro-2'-deoxycytidine.
G at positions 9, 15, 17, and 31 is 2'-O-Methyl-2'-deoxyguanosine.
A at position 22 is 2'-O-Methyl-2'-deoxyadenosine.

NX31976 40K PEG

SEQ ID NO:2

C at positions 4, 8, 21 and 29 is 2'-fluoro-2'-deoxycytidine.
U at positions 6, 20 and 30 is 2'-fluoro-2'-deoxyuridine.
G at positions 5, 9, 17, and 31 is 2'-O-Methyl-2'-deoxyguanosine.
A at position 22 is 2'-O-Methyl-2'-deoxyadenosine.

METHOD FOR TREATMENT OF TUMORS USING NUCLEIC ACID LIGANDS TO PDGF

RELATED APPLICATIONS

This application claims the benefit of U.S. Provisional Application Serial No. 60/205,006, filed May 17, 2000. This application is also a continuation in part of U.S. Ser. No. 08/479,725 filed Jun. 7, 1995 now U.S. Pat. No. 5,674,685, issued Oct. 7, 1997, U.S. Ser. No. 08/479,783 now filed Jun. 7, 1995 U.S. Pat. No. 5,668,264, issued Sep. 16, 1997 and U.S. Ser. No. 08/618,693 now filed Mar. 20, 1996 U.S. Pat. No. 5,723,594, issued Mar. 3, 1998, each entitled "High Affinity PDGF Nucleic Acid Ligands," and U.S. Ser. No. 08/991,743 filed Dec. 16, 1997 now U.S. Pat. No. 6,229,002, issued, May 8, 2001, entitled "Platelet Derived Growth Factor (PDGF) Nucleic Acid Ligand Complexes."

FIELD OF THE INVENTION

This invention relates generally to a method for increasing the uptake of drugs into tumors by treatment with a nucleic acid ligand to PDGF in combination with a cytotoxic agent. The method used for identifying nucleic acid ligands to PDGF is called SELEX, an acronym for Systematic Evolution of Ligands by Exponential enrichment. The method of the present invention is useful for increasing the therapeutic effectiveness of cytotoxic agents.

BACKGROUND OF THE INVENTION

The Systematic Evolution of Ligands by Exponential Enrichment (SELEX) process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096, entitled "Nucleic Acid Ligands," and U.S. Pat. No. 5,270,163 (see also WO 91/19813), entitled "Methods for Identifying Nucleic Acid Ligands," each of which is specifically incorporated herein by reference in its entirety. Each of these applications, collectively referred to herein as the SELEX Patent Applications, describes a fundamentally novel method for making a nucleic acid ligand to any desired target molecule.

The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. Nos. 5,763,177 and 6,011,577, both entitled "Systematic Evolution of Ligands by Exponential Enrichment: Photoselection of Nucleic Acid Ligands and Solution SELEX," describe a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588, entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459, entitled "Systematic Evolution of Ligands by EXponential Enrichment: Chimeric SELEX,"

and U.S. Pat. No. 5,683,867, entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. Pat. No. 6,011,020, entitled "Nucleic Acid Ligand Complexes." Each of the above described patent applications which describe modifications of the basic SELEX procedure are specifically incorporated by reference herein in their entirety.

One approach to increasing the effectiveness of existing anti-cancer drugs for the treatment of solid malignancies is to augment the uptake of the drugs into tumors, and thereby obtain increased therapeutic concentration without elevating the adverse side-effects. Most solid tumors display an increased interstitial fluid pressure (IFP). The molecular mechanisms causing increased tumor IFP are poorly understood. However, tumor stroma involvement in IFP control has been demonstrated. (Gullino et al. (1964) Cancer Res. 24:780–797; Philips et al. (1990) J. Natl Cancer Inst. 82:1457–1469; Jain (1987) Cancer Res. 47:3039–3051). It has been suggested that high tumor IFP prevents drug transport from the circulation into the tumor interstitium. The reduction of tumor IFP therefore is a target for efforts to increase tumor drug uptake. (Jain (1996) Science 271:1079–1080). Several agents which induce a lowering of IFP, and thereby increase the transcapillary transport in experimental murine tumors have been identified, including nicotinamide (Lee et al. (1992) Cancer Res. 52:3237–3240), TNF-α (Kristensen et al. (1996) Br. J. Cancer 74:533–536) and dexamethasone (Kristjansen et al. (1993) Cancer Res. 53:4764–4766).

Platelet-derived growth factor (PDGF) and the cognate tyrosine kinase receptors are potent mitogens for mesenchymal cells. In addition to its growth promoting effects, PDGF-BB is involved also in the regulation of IFP. After dextran-induced anaphylaxis and lowering of IFP in rat skin, local administration of PDGF-BB results in normalized IFP. PDGF receptors are expressed in the tumor stroma of many common solid tumors, e.g. lung, colon and breast carcinomas. Based on these observations the effects of PDGF antagonists on tumor IFP, tumor transcapillary transport and therapeutic effects of cytotoxic drugs were investigated.

SUMMARY OF THE INVENTION

The present invention includes a method for treating tumors, more specifically, solid tumors comprising administering to a host a therapeutically effective dose of a composition comprising a PDGF aptamer and a cytotoxic agent. In a preferred embodiment the PDGF aptamer is identified using the SELEX process for the Systematic Evolution of Ligands by EXponential enrichment. The present invention also includes a method for reducing the interstitial fluid pressure (IFP) of a tumor, more specifically, a solid tumor comprising administering a PDGF nucleic acid ligand. Finally, the present invention includes a method for increasing the uptake of cytotoxic agents into a tumor comprising administering to a host a composition comprising a PDGF aptamer and a cytotoxic agent. The present invention provides a novel method to increase drug uptake and therefore the therapeutic effectiveness of chemotherapy, by treatment with a PDGF inhibitor in conjunction with the therapeutic agent. As illustrated below, treatment with a PDGF aptamer decreases interstitial hypertension in these tumors thereby increasing the uptake of the therapeutic agent.

DETAILED DESCRIPTION OF THE INVENTION

Figure 1A:
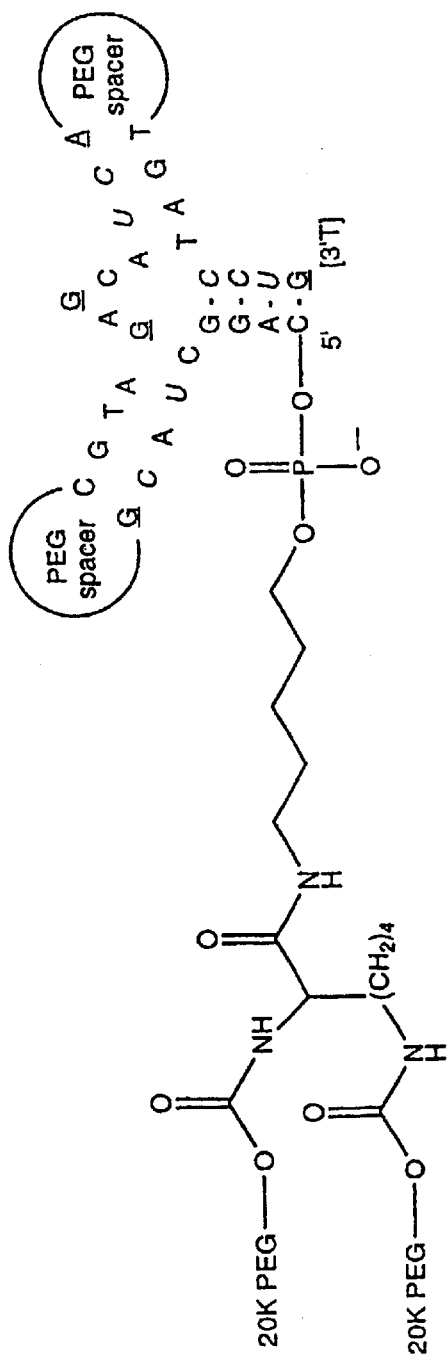
FIGS. 1A and B show the molecular description of the PDGF aptamer used in the present study ((SEQ ID NO:1), FIG. 1A) and the aptamer that was used as the control. ((SEQ ID NO:2), FIG. 1B).
Figure 1A:
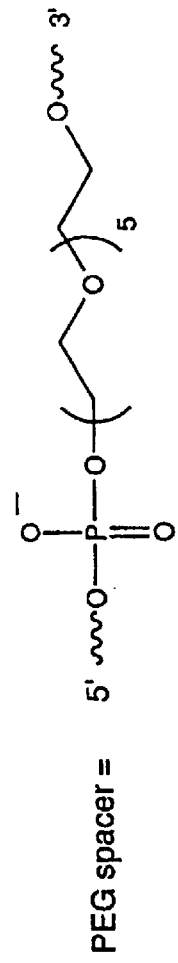

Various terms are used herein to refer to aspects of the present invention. To aid in the clarification of the description of the components of this invention, the following definitions are provided.

As used herein a "nucleic acid ligand" is a non-naturally occurring nucleic acid having a desirable action on a target. Nucleic acid ligands are often referred to as "aptamers." A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In a preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand does not have the known physiological function of being bound by the target molecule. In the present invention, the target is PDGF or regions thereof. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein a "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands that interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology was employed to obtain nucleic acid ligands to PDGF. See U.S. Pat. No. 5,674,685, issued Oct. 7, 1997, U.S. Pat. No. 5,668,264, issued Sep. 16, 1997 and U.S. Pat. No. 5,723,594, issued Mar. 3, 1998, each entitled "High Affinity PDGF Nucleic Acid Ligands," and U.S. Pat. No. 6,229,002, issued, May 8, 2001, entitled "Platelet Derived Growth Factor (PDGF) Nucleic Acid Ligand Complexes."

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX target was PDGF.

A "cytotoxic agent" is any substance used to destroy tumor cells. The method of this invention can be used with any systemically administered cytotoxic agent including, but not limited to, Bleomycin, Cisplatin, and Pt analogues; Carboplatin and Iproplatin, Cyclophosphamide, Daunorubicin, Doxofluoridine, Doxorubicin, Etoposide, Epirubicin, 5-Flurouracil, Gemzar, Ifosfamide, Melphalan, Methotrexate, Mithramycin, Mitomycin C, Mitoxanthrone, Streptozotocin, Taxol and Taxotere, Vincristine, Vinblastine, Vindesine, Vinorelbine, Topotecan and CPT-11.

"Therapeutic" as used herein, includes treatment and/or prophylaxis. When used, therapeutic refers to humans, as well as, other animals.

"Pharmaceutically or therapeutically effective dose or amount" refers to a dosage level sufficient to induce a desired biological result. That result may be the delivery of a pharmaceutical agent, alleviation of the signs, symptoms or causes of a disease or any other desirous alteration of a biological system.

A "host" is a living subject, human or animal, into which a drug or cytotoxic agent is administered.

Note, that throughout this application various citations are provided. Each citation is specifically incorporated herein in its entirety by reference.

The present invention includes a method for treating solid tumors comprising administering to a host a therapeutically effective dose of a composition comprising a PDGF aptamer and a cytotoxic agent. In a preferred embodiment the PDGF aptamer is identified using the SELEX methodology. The SELEX process is described in U.S. patent application Ser. No. 07/536,428, entitled "Systematic Evolution of Ligands by Exponential Enrichment," now abandoned, U.S. Pat. No. 5,475,096, entitled "Nucleic Acid Ligands," and U.S. Pat. No. 5,270,163 (see also WO 91/19813), entitled "Methods for Identifying Nucleic Acid Ligands." These applications, each specifically incorporated herein by reference, are collectively called the SELEX Patent Applications.

The SELEX process provides a class of products that are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps.

1. A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below; (b) to mimic a sequence known to bind to the target; or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2. The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3. The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4. Those nucleic acids selected during partitioning as having the relatively higher affinity for the target are then amplified to create a new candidate mixture that is enriched in nucleic acids having a relatively higher affinity for the target.

5. By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. Nos. 5,763,177 and 6,001,577, both entitled "Systematic Evolution of Ligands by Exponential Enrichment: Photoselection of Nucleic Acid Ligands and Solution SELEX," all describe a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588, entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938, entitled "Nucleic Acid Ligands to HIV-RT and HIV-1 Rev," describes methods for obtaining improved nucleic acid ligands after SELEX has been performed. U.S. Pat. No. 5,705,337, entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459, entitled "Systematic Evolution of Ligands by Exponential Enrichment: Chimeric SELEX," and U.S. Pat. No. 5,683,867, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938, methods are described for obtaining improved nucleic acid ligands after the SELEX process has been performed. This patent, entitled "Nucleic Acid Ligands to HIV-RT and HIV-1 Rev," is specifically incorporated herein by reference.

One potential problem encountered in the diagnostic use of nucleic acids is that oligonucleotides in their phosphodiester form may be quickly degraded in body fluids by intracellular and extracellular enzymes, such as endonucleases and exonucleases, before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned and U.S. Pat. No. 5,660,985, both entitled "High Affinity Nucleic Acid Ligands Containing Modified Nucleotides," and U.S. patent application Ser. No. 09/362,578, filed Jul. 28, 1999, entitled "Transcription-free SELEX," each of which is specifically incorporated herein by reference in its entirety. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases, isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands to PDGF of the invention are prepared through the SELEX methodology that is outlined above and thoroughly enabled in the SELEX applications incorporated herein by reference in their entirety.

As noted above, the cytotoxic agent can be any substance used in the prevention, diagnosis, alleviation, treatment or cure of disease. More specifically, the cytotoxic agent can be selected from any systemically administrated agent including, but not limited to, Bleomycin, Cisplatin, and Pt analogues; Carboplatin and Iproplatin, Cyclophosphamide, Daunorubicin, Doxofluoridine, Doxorubicin, Etoposide, Epirubicin, 5-Flurouracil, Gemzar, Ifosfamide, Melphalan, Methotrexate, Mithramycin, Mitomycin C, Mitoxanthrone, Streptozotocin, Taxol and Taxotere, Vincristine, Vinblastine, Vindesine, Vinorelbine, Topotecan and CPT-11.

Various delivery systems are known in the art and can be used to administer the therapeutic composition comprising the PDGF aptamer and cytotoxic agent of the invention, e.g., aqueous solution, encapsulation in liposomes, microparticles, and microcapsules.

Therapeutic compositions of the invention may be administered parenterally by injection, although other effective administration forms, such as intraarticular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and the nucleic acid ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing the compositions for systemic delivery may be via subcutaneous, intramuscular, intravenous, intranasal or vaginal or rectal suppository.

The amount of the composition which will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curved derived from in vitro or animal model test systems. For example, an effective amount of the composition of the invention is readily determined by administering graded doses of the composition of the invention and observing the desired effect.

The following examples are provided to explain and illustrate the present invention and are not intended to be limiting of the invention.

Figure 1B:
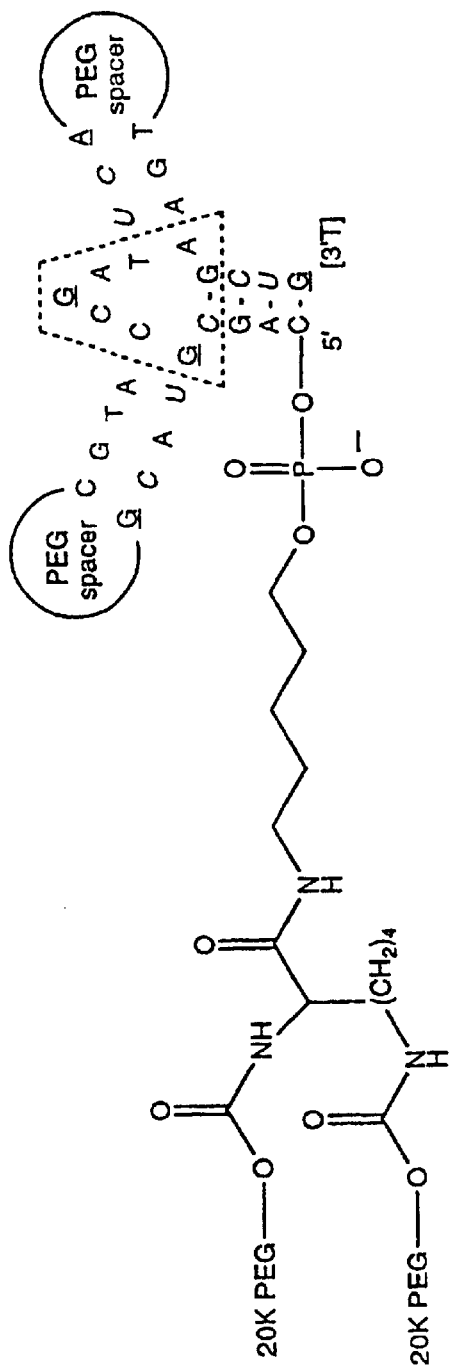
Figure 1B:
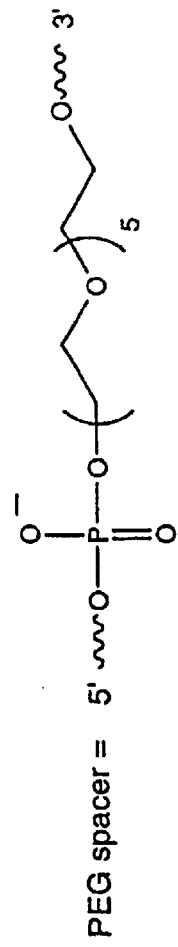

The PDGF-B aptamer used in the present study ((SEQ ID NO:1), FIG. 1A) was produced by the SELEX method. (Tuerk and Gold (1990) Science 249:505–510, which is incorporated herein by reference in its entirety). The modified DNA aptamer, linked to 40 kDa polyethylene glycol, has a high affinity for PDGF-B with a Kd of ~0.1 nM. (Green et al. (1996) Biochemistry 35:14413–14424; Floege et al. (1999) Am. J. Pathol. 154:169–179; U.S. Pat. No. 6,229,002, issued May 8,2001, ((SEQ ID NO:146), FIG. 9A), each of which is incorporated herein by reference in its entirety). A sequence-scrambled analog of the PDGF-B aptamer was used as a control. ((SEQ ID NO:2), FIG. 1B). This oligonucleotide has a Kd for PDGF-BB in the micromolar range. (Floege et al. (1999) Am. J. Pathol. 154:169–179; U.S. Pat. No. 6,229,002, issued May 8, 2001, ((SEQ ID NO:147), FIG. 9B)).

Figure 2:
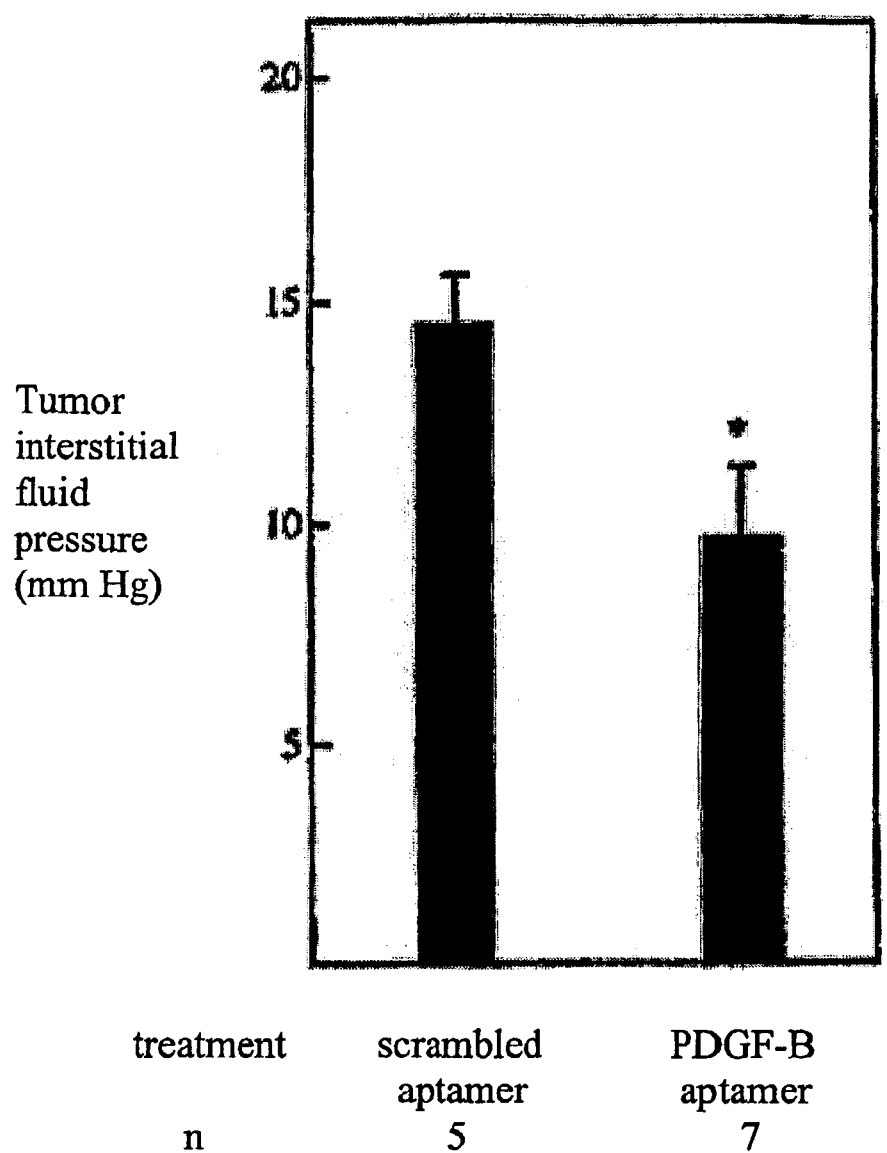
FIG. 2 illustrates graphically the reduction in tumor interstitial fluid pressure (IFP) upon treatment of PROb tumors with a PDGF specific aptamer. Average tumor IFP in the animals treated with a sequence-scrambled control oligonucleotide (n=5) and PDGF-B specific aptamer (n=7) is depicted. Bars represent S.E.M; * p<0.05

Example 1 describes the method used to treat PROb tumor-bearing rats with the PDGF-B specific aptamer. As can be seen in FIG. 2 treatment of PROb tumor-bearing rats with the PDGF-B specific aptamer resulted in a decrease in tumor IFP when compared to rats treated with the control aptamer. The mean IFP in control aptamer-treated tumors was 14.6±1.2 mm Hg (±S.E.M.) and 9.7±1.6 mm Hg (±S.E.M.) in tumors treated with the PDGF-B specific aptamer. The method used to determine IFP is described in Example 2.

Figure 3:
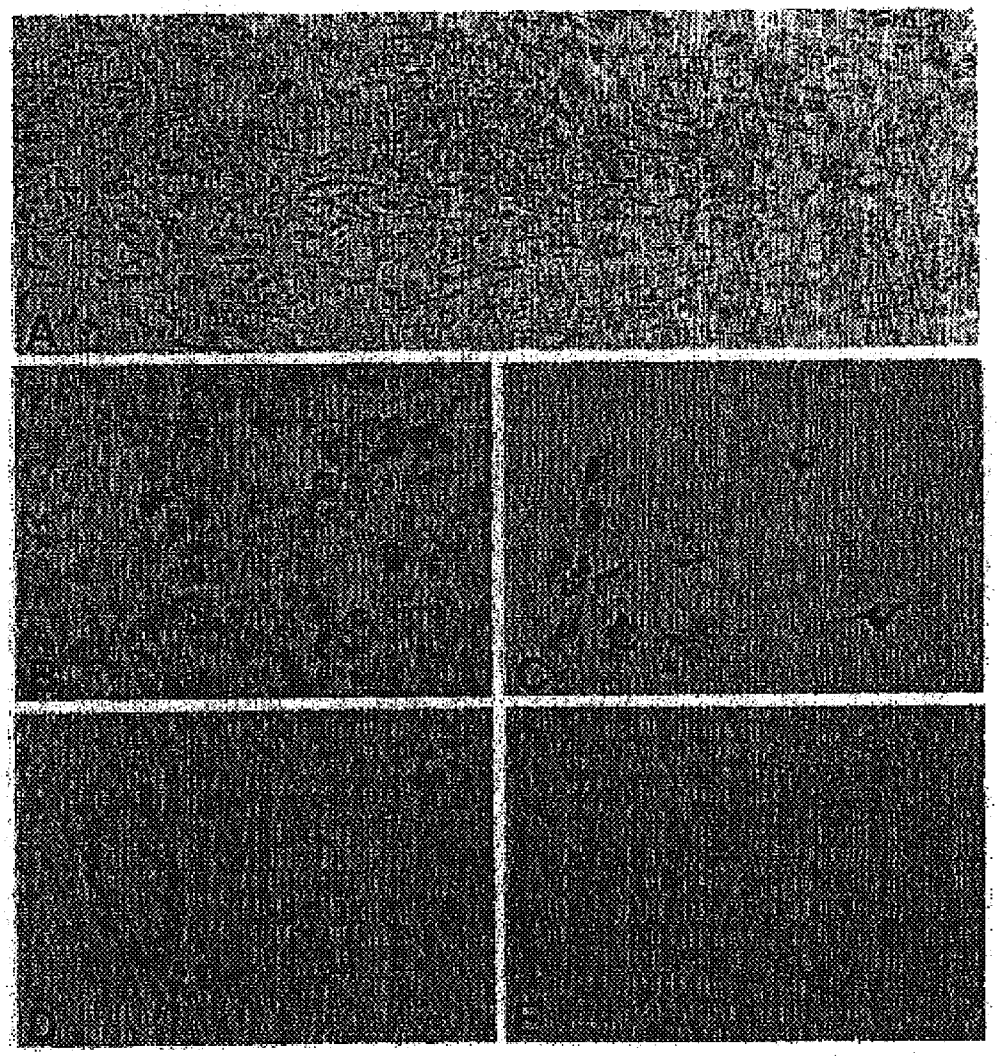
FIG. 3 depicts the distribution of PDGF β-receptors and PDGF-AB/BB in PROb tumors. Morphological analysis of sections from PROb tumor cells revealed three discrete zones in the investigated tumors (FIG. 3A). Towards the exterior a cell rich zone containing proliferative cells arranged in glandular structures was evident. A zone further towards the central part of the tumors contained apoptotic cells and cell debris, whereas the central parts were largely acellular, but contained extracellular matrix deposits. Inflammatory infiltrates were not evident in the investigated tumors. Immunohistochemical analyses showed that PDGF-AB/BB was expressed in blood vessels (FIG. 3B) and in the central parts of tumors by cells morphologically identified as macrophages (FIG. 3C). A weak but clearly visible staining of PDGF β-receptors was present in stromal structures in large parts of the tumors, especially around tumor glands (FIG. 3D). PDGF β-receptor staining was completely blocked by addition of a peptide corresponding to the amino acids 981–994 of the human/murine PDGF β-receptor at a 10-fold molar excess to the anti-PDGF β-receptor antibody (FIG. 3E).

PROb tumors were analyzed with regard to morphology, as well as distribution of PDGF-AB/BB and PDGF β-receptors as described in Example 3. The tumors displayed a heterogeneous morphology. At the tumor periphery, tumor cells were arranged in glandular structures, whereas more centrally, tumor cells were less abundant and less well organized (FIG. 3A). The central part was basically acellular (FIG. 3A). Expression of PDGF-AB/BB in PROb tumors was found in blood vessels and possibly in extravascular stromal cells surrounding tumor glands (FIG. 3B). In the central part of the tumors, few if any tumor cells were present, but strongly PDGF-AB/BB positive cells were seen (FIG. 3C). In no part of the tumors could PDGF-AB/BB positive tumor cells be clearly discerned. PDGF β-receptors were found in vascular cells of larger vessels, and in unidentified, possibly microvascular, cells in the stroma (FIG. 3D). The absence of PDGF-AB/BB and β-receptor expression by carcinoma cells in PROb tumors, is in agreement with the characteristics of cultured PROb cells (data not shown).

Figure 4:
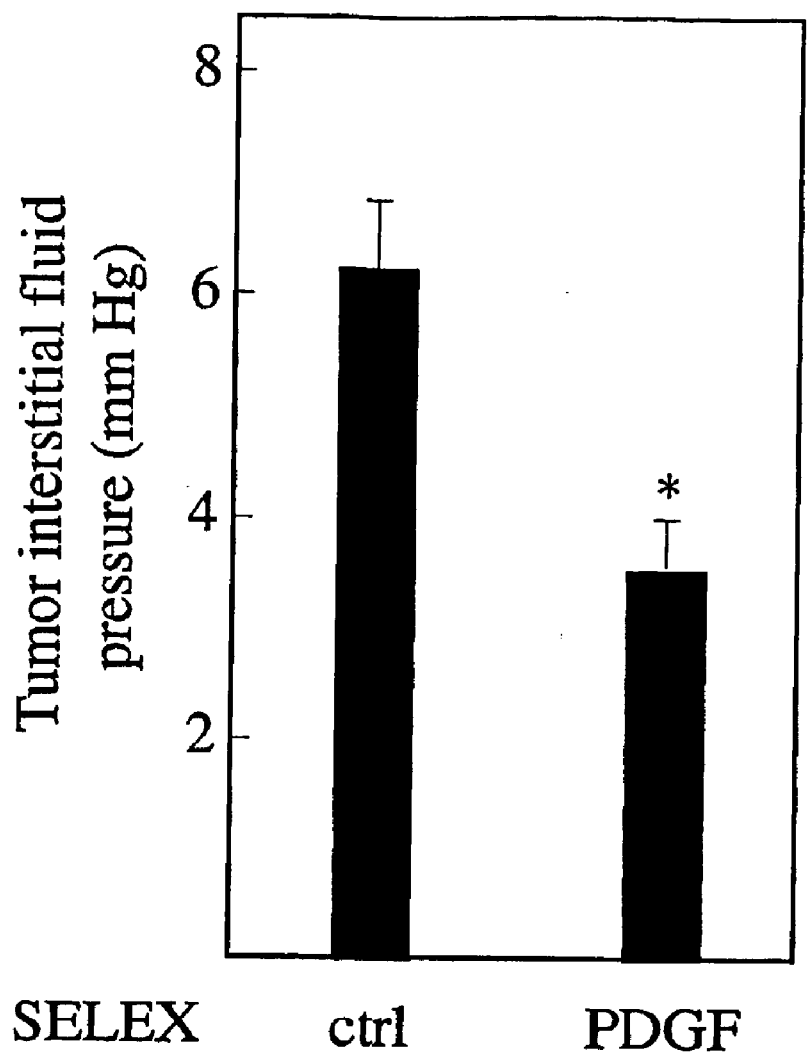
FIG. 4 illustrates graphically the reduction of IFP upon treatment of SCID-Mice bearing subcutaneous KAT-4 tumors (human anaplastic thyroid carcinoma with PDGF aptamers.
Figure 5:
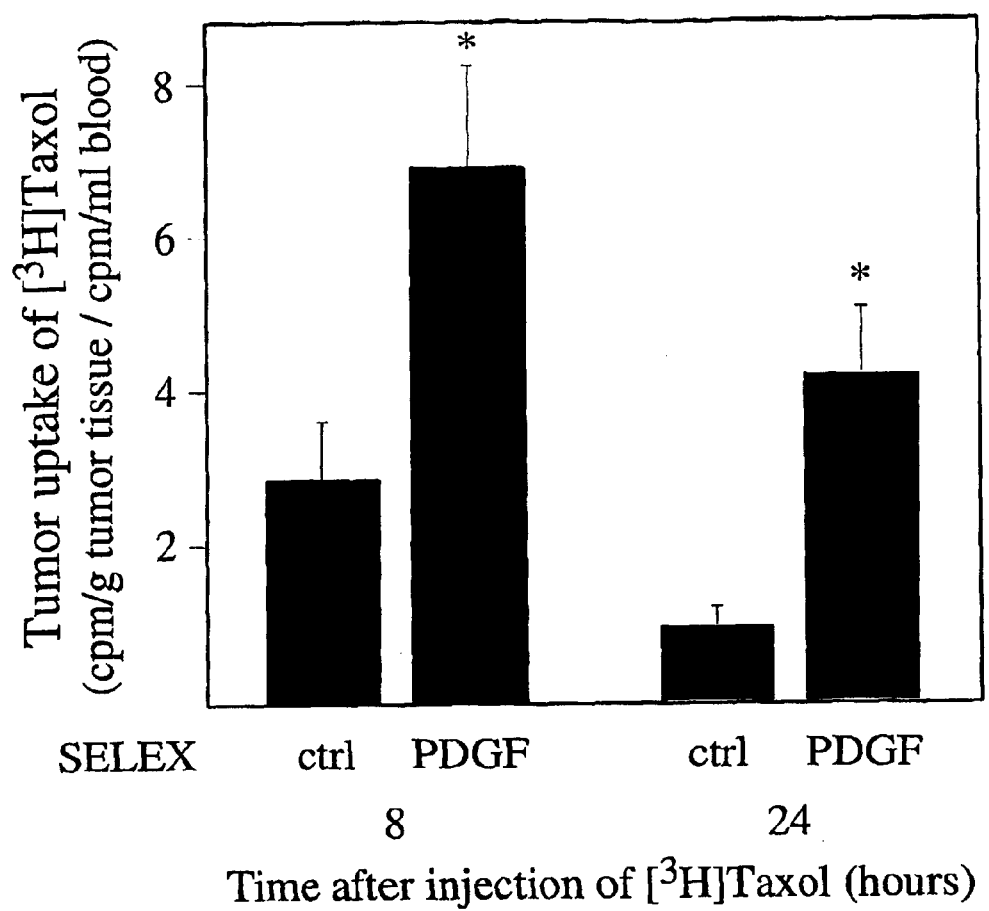
FIG. 5 illustrates graphically the increased uptake of the chemotherapeutic agent Taxol upon pretreatment of KAT-4 tumors with PDGF aptamers.

Prompted by these findings, the effects of treatment with PDGF aptamer (SEQ ID NO:1) were tested on the KAT-4 tumor model (Examples 4 and 5). Both of these tumor models showed PDGF receptor expression in tumor stroma but not on tumor cells. As can be seen in FIGS. 4 and 5 treatment with PDGF aptamers lowers IFP in KAT-4 tumors and increases the uptake of Taxol.

EXAMPLES

Materials and Methods

Tissue culture. Cells were cultured under standard conditions and all tissue culture media were supplemented with 10% fetal bovine serum (FBS) and antibiotics, unless otherwise stated. PAE cells were maintained in F12 culture medium (Sigma). PROb cells were kept in Dulbecco's Modified Eagle's Medium (Sigma).

PDGF/PDGF receptor inhibitors. The PDGF-B aptamer used in the present study was produced by the Systematic Evolution of Ligands by Exponential Enrichment (SELEX) method. (Tuerk and Gold (1990) Science 249:505–510, which is incorporated herein by reference in its entirety).

The modified DNA aptamer, linked to 40 kDa polyethylene glycol, has a high affinity for PDGF-B with a Kd of ~0.1 nM. (Green et al. (1996) Biochemistry 35:14413–14424; Floege et al. (1999) Am. J. Pathol. 154:169–179, each of which is incorporated herein by reference in its entirety). The aptamer shows biphasic clearance in rats following iv injection, approximately 47% is cleared with a half-life of 32 minutes, while the remainder is cleared with a half-life of 135 minutes. (Floege et al. (1999) Am. J. Pathol. 154:169–179). As a control, a sequence-scrambled analog of the PDGF-B aptamer was used. This oligonucleotide has a Kd for PDGF-BB in the micromolar range. (Floege et al. (1999) Am. J. Pathol. 154:169–179).

Example 1
Tumor Establishment and Treatment of PROb Tumors with PDGF Inhibitors Subcutaneously growing PROb tumors (Martin et al. (1996) Int. J. Cancer 65:796–804) were established in BDIX rats by injection of $5\times10^6$ tumor cells in 50 µL of PBS in the flank. The rats were kept under pathogen-free conditions and were fed ad libitum. They were monitored regularly for tumor growth and experiments were performed 8–12 weeks after tumor cell implantation on rats bearing tumors ranging in size between 0.6 $cm^3$ and 7.6 $cm^3$. The PDGF-B specific aptamer, and a control aptamer (see above), were given as i.p. injections in 2 mL PBS twice daily for 4 consecutive days at a dose of 7 $mg\times kg^{-1}\times day^{-1}$. All animal experiments described in the present report were approved by the Ethical Committee for Animal Experiments in Uppsala, Sweden.

Example 2
Measurement of Tumor IFP

Tumor IFP was measured using the wick-in-needle technique (Wiig et al. (1982) Scan. J. Clin. Lab. Invest. 42:159–164). Briefly, rats were anaesthetized using isofluran in a mixture of $O_2$ and air. A standard 23-gauge needle filled with nylon-floss and saline, supplemented with 50 IE/mL of heparin was inserted into the center of the tumor and connected to a pressure transducer. This makeup enables continuous and stable recordings of fluid pressure. Fluid communication between the needle and the transducer was confirmed by compression and decompression of the tubing during each measurement. Tumor IFP was measured once before treatment with PDGF aptamers, and again 1–2 hours after the last administration of aptamers or vehicle alone. The change in tumor IFP was calculated for each tumor. After the second IFP measurement the rats were sacrificed and the tumors were excised and snap frozen in liquid nitrogen for further analyses.

Example 3
Immunohistochemistry

For routine morphology, paraffin-embedded 4 µm sections were stained with van Gieson staining. Immunohistochemistry was performed on 6 µm cryosections from PROb tumors. Sections were fixed in acetone and blocked with 0.3% hydrogen peroxide in methanol for 15 minutes, rinsed and further incubated in a solution containing 20% human normal serum in a buffer containing 2% rat serum, 3% bovine serum albumin, 0.01% NP40 in PBS (RM buffer) for 5 hours at 4° C. Primary antibodies dissolved in RM buffer were added, either 4 µg/mL affinity-purified rabbit anti-PDGF β-receptor IgG (Claesson-Welsh et al. (1988) Mol. Cell Biol. 8:3476–3486) for 5 hours at 4° C., or overnight at 4° C. with 1.3 µg/mL of the monoclonal mouse anti-PDGF-AB/BB IgG (PGF 007, Mochida Pharmaceutical Company, Tokyo, Japan). Sections were rinsed in PBS with 0.01% NP40. Bound IgG was detected with biotinylated goat anti-rabbit or biotinylated rabbit anti-mouse antibodies, respectively. Sections were developed with a Vectastain ABC elite kit (Vector, Burlingame, Calif.) using amino-ethyl-carbazole as a chromophore. Sections were counter-stained with Mayer's hematoxylin for 30 seconds.

Example 4
Treatment of KAT-4 Tumors with PDGF Inhibitors

SCID-mice bearing subcutaneous KAT-4 tumors (human, anaplastic thyroid carcinoma) were pre-treated for 4 consecutive days with 12 $mg\times kg^{-1}\times day^{-1}$ SELEX aptamers (i.p. injections, three times daily). Tumor interstitial fluid pressure was measured using the wick-in-needle technique. The results are set forth in FIG. 4. * $p<0.05$, Student's t-test.

Example 5
Treatment of KAT-4 Tumors with a PDGF Inhibitor in Combination with the Cytotoxic Agent Taxol SCID-mice bearing subcutaneous KAT-4 tumors (human, anaplastic thyroid carcinoma) were pre-treated for 4 consecutive days with 12 $mg\times kg^{-1}\times day^{-1}$ SELEX aptamers (i.p. injections, three times daily). [$^3$H]Taxol was injected s.c at a site distant from the tumor and in a mix of 5 $mg\times kg^{-1}$ unlabelled Taxol. Eight or 24 hours following injection of radiolabelled drug, blood was sampled, animals were sacrificed and tumors and 4 other tissues were excised. Subsequently, tissues were weighed and homogenized in a RIPA lysis buffer and the amount radioactivity in each sample was determined in a scintillation counter. Tumor uptake of Taxol was expressed as cpm/g tumor tissue divided by cpm/ml blood. The results are set forth in FIG. 5. * $p<0.05$, Student's t-test.

Statistical analysis. Statistical analysis was performed using the paired or unpaired two-sided Student's t-test. A p-value$<0.05$ was considered statistically significant.

What is claimed is:

1. A method for treating tumors comprising administering to a host having a tumor a therapeutically effective dose of a composition comprising a platelet-derived growth factor (PDGF) aptamer and a cytotoxic agent, whereby tumors are treated.

2. The method of claim 1 wherein said PDGF aptamer is identified according to a method comprising:

a) preparing a candidate mixture of nucleic acids;

b) contacting the candidate mixture of nucleic acids with PDGF, wherein nucleic acids having an increased affinity to PDGF relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acids with relatively higher affinity and specificity for binding to PDGF, whereby a nucleic acid ligand of PDGF may be identified.

3. The method of claim 1 wherein said PDGF aptamer is SEQ ID NO:1.

4. The method of claim 1 wherein said cytotoxic agent is selected from the group consisting of Bleomycin, Cisplatin, and Pt analogues; Carboplatin and Iproplatin, Cyclophosphamide, Daunorubicin, Doxofluoridine, Doxorubicin, Etoposide, Epirubicin, 5-Flurouracil, Gemzar, Ifosfamide, Melphalan, Methotrexate, Mithramycin, Mitomycin C, Mitoxanthrone, Streptozotocin, Taxol and Taxotere, Vincristine, Vinblastine, Vindesine, Vinorelbine, Topotecan and CPT-11.

5. A method for reducing the interstitial fluid pressure (IFP) of a tumor comprising administering a PDGF aptamer to a host having a tumor, whereby the intestinal fluid pressure of a tumor is reduced.

6. The method of claim 5 wherein said PDGF aptamer is identified according to a method comprising:

a) preparing a candidate mixture of nucleic acids;

b) contacting the candidate mixture of nucleic acids with PDGF, wherein nucleic acids having an increased affinity to PDGF relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acids with relatively higher affinity and specificity for binding to PDGF, whereby a nucleic acid ligand of PDGF may be identified.

7. The method of claim 5 wherein said PDGF aptamer is SEQ ID NO:1.

8. A method for increasing the uptake of cytotoxic agents into a tumor comprising administering to a host having a tumor a composition comprising a PDGF aptamer and a cytotoxic agent, whereby the uptake of cytotoxic agents into the tumor is increased.

9. The method of claim 8 wherein said PDGF aptamer is identified according to a method comprising:

a) preparing a candidate mixture of nucleic acids;

b) contacting the candidate mixture of nucleic acids with PDGF, wherein nucleic acids having an increased affinity to PDGF relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acids with relatively higher affinity and specificity for binding to PDGF, whereby a nucleic acid ligand of PDGF may be identified.

10. The method of claim 8 wherein said PDGF aptamer is SEQ ID NO:1.

11. The method of claim 8 wherein said cytotoxic agent is selected from the group consisting of Bleomycin, Cisplatin, and Pt analogues; Carboplatin and Iproplatin, Cyclophosphamide, Daunorubicin, Doxofluoridine, Doxorubicin, Etoposide, Epirubicin, 5-Flurouracil, Gemzar, Ifosfamide, Melphalan, Methotrexate, Mithramycin, Mitomycin C, Mitoxanthrone, Streptozotocin, Taxol and Taxotere, Vincristine, Vinblastine, Vindesine, Vinorelbine, Topotecan and CPT-11.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
     Nucleic Acid Ligand -continued

```
<221> NAME/KEY: modified_base
<222> LOCATION: (6)..(30)
<223> OTHER INFORMATION: U at positions 6, 20 and 30 is
      2'-fluoro-2'-deoxyuridine
<221> NAME/KEY: modified_base
<222> LOCATION: (8)..(29)
<223> OTHER INFORMATION: C at positions 8, 21, 28, and 29 is
      2'-fluoro-2'-deoxycytidine
<221> NAME/KEY: modified_base
<222> LOCATION: (9)..(31)
<223> OTHER INFORMATION: G at positions 9, 15, 17, and 31 is
      2'-O-Methyl-2'-deoxyguanosine
<221> NAME/KEY: modified_base
<222> LOCATION: (22)
<223> OTHER INFORMATION: A at position 22 is
      2'-O-Methyl-2'-deoxyadenosine
<221> NAME/KEY: modified_base
<222> LOCATION: (1)..(30)
<223> OTHER INFORMATION: The residues at positions 9 and 10 are
      connected by a hexaethylene glycol phosphoramidite linker. The
      residues at positions 21 and 22 are connected by a hexaethylene
      glycol phosphoramidite linker.
<221> NAME/KEY: modified_base
<222> LOCATION: (32)
<223> OTHER INFORMATION: Nucleotide 32 is an inverted orientation T
      (3'-3'-linked)

<400> SEQUENCE: 1
caggcuacgc gtagagcauc atgatccugt                              30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (4)..(29)
<223> OTHER INFORMATION: C at positions 4, 8, 21 and 29 is
      2'-fluoro-2'-deoxycytidine
<221> NAME/KEY: modified_base
<222> LOCATION: (6)..(30)
<223> OTHER INFORMATION: U at positions 6, 20 and 30 is
      2'-fluoro-2'-deoxyuridine
<221> NAME/KEY: modified_base
<222> LOCATION: (5)..(31)
<223> OTHER INFORMATION: G at positions 5, 9, 17, and 31 is
      2'-O-Methyl-2'-deoxyguanosine
<221> NAME/KEY: modified_base
<222> LOCATION: (22)
<223> OTHER INFORMATION: A at position 22 is
      2'-O-Methyl-2'-deoxyadenosine
<221> NAME/KEY: modified_base
<222> LOCATION: (1)..(30)
<223> OTHER INFORMATION: The residues at positions 9 and 10 are
      connected by a hexaethylene glycol phosphoramidite linker. The
      residues at positions 21 and 22 are connected by a hexaethylene
      glycol phosphoramidite linker.
<221> NAME/KEY: modified_base
<222> LOCATION: (32)
<223> OTHER INFORMATION: Nucleotide 32 is an inverted orientation T
      (3'-3'-linked)

<400> SEQUENCE: 2
cagcguacgc gtaccgatuc atgaagcugt                              30
```